United States Patent
Noguchi (10) Patent No.: US 12,127,884 B2
(45) Date of Patent: Oct. 29, 2024

(54) ULTRASOUND PROBE

(71) Applicant: FUJIFILM Corporation, Tokyo (JP)

(72) Inventor: Shinsuke Noguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 597 days.

(21) Appl. No.: 17/155,477

(22) Filed: Jan. 22, 2021

(65) Prior Publication Data

US 2021/0137496 A1 May 13, 2021

Related U.S. Application Data (63) Continuation of application No. PCT/JP2019/028521, filed on Jul. 19, 2019.

(30) Foreign Application Priority Data

Jul. 25, 2018 (JP) .................................. 2018-139274

(51) Int. Cl.
*A61B 8/00* (2006.01)
*C08L 55/02* (2006.01)

(52) U.S. Cl.
CPC .......... *A61B 8/4472* (2013.01); *A61B 8/4427* (2013.01); *A61B 8/4483* (2013.01); *A61B 8/56* (2013.01); *C08L 55/02* (2013.01); *C08L 2201/02* (2013.01); *C08L 2203/14* (2013.01)

(58) Field of Classification Search
None
See application file for complete search history.

(56) References Cited

U.S. PATENT DOCUMENTS

| | | | | |
|---|---|---|---|---|
| 4,992,481 | A * | 2/1991 | von Bonin | C09K 21/14 521/54 |
| 6,045,883 | A * | 4/2000 | Akiyama | C08L 23/12 525/92 D |
| 8,792,658 | B2 * | 7/2014 | Baliga | G08B 21/16 381/189 |
| 2002/0018932 | A1 * | 2/2002 | Chikada | H01M 50/209 429/185 |

(Continued)

FOREIGN PATENT DOCUMENTS

| | | |
|---|---|---|
| CN | 103417244 A | 12/2013 |
| JP | 2005-320365 A | 11/2005 |

(Continued)

OTHER PUBLICATIONS

Pay attention to the recharging of lithium polymer batteries for models!, Documents of the press release of the Tokyo Fire Department, May 23, 2013, Tokyo Fire Department.

(Continued)

*Primary Examiner* — Jonathan Cwern
(74) *Attorney, Agent, or Firm* — Studebaker & Brackett PC (57) ABSTRACT

An ultrasound probe 11 includes a housing 12, a transducer array 13 that is retained in the housing 12 and has a rear surface portion 13B, from which a wiring cable WC1 is drawn out, a circuit substrate 15 that is retained in the housing 12, the wiring cable WC1 being connected to the circuit substrate 15, a battery 14 that is retained in the housing 12 and performs power supply, and a fire protection structure that is disposed between the transducer array 13 and the circuit substrate 15 in the housing 12.

10 Claims, 7 Drawing Sheets

(56) References Cited

U.S. PATENT DOCUMENTS

| | | | | |
|---|---|---|---|---|
| 2006/0275666 | A1* | 12/2006 | Chang | H01M 10/4235 |
| | | | | 429/223 |
| 2010/0160785 | A1 | 6/2010 | Poland et al. | |
| 2013/0064037 | A1* | 3/2013 | Cerofolini | A61B 8/565 |
| | | | | 367/7 |
| 2013/0301395 | A1* | 11/2013 | Hebrard | A61B 8/546 |
| | | | | 367/189 |

FOREIGN PATENT DOCUMENTS

| | | |
|---|---|---|
| JP | 2010-528698 A | 8/2010 |
| JP | 2013-027667 A | 2/2013 |
| JP | 2015-153476 A | 8/2015 |
| JP | 2015-163684 A | 9/2015 |
| JP | 2015-211726 A | 11/2015 |
| WO | 2015/115154 A1 | 8/2015 |

OTHER PUBLICATIONS

International Search Report issued in PCT/JP2019/028521; mailed Oct. 15, 2019.

International Preliminary Report On Patentability and Written Opinion issued in PCT/JP2019/028521; issued Jan. 26, 2021.

An Office Action; "Notice of Reasons for Refusal", mailed by the Japanese Patent Office on Aug. 3, 2021, which corresponds to Japanese Patent Application No. 2020-532360 and is related to U.S. Appl. No. 17/155,477; with English language translation.

The extended European search report issued by the European Patent Office on Aug. 13, 2021, which corresponds to European Patent Application No. 19839929.7-1126 and is related to U.S. Appl. No. 17/155,477.

An Office Action mailed by the Chinese Patent Office on Jan. 27, 2024, which corresponds to Chinese Patent Application No. 201980049253.9 and is related to U.S. Appl. No. 17/155,477.

An Office Action mailed by the Chinese Patent Office on Oct. 21, 2023, which corresponds to Chinese Patent Application No. 201980049253.9 and is related to U.S. Appl. No. 17/155,477.

An Office Action mailed by China National Intellectual Property Administration on Jun. 17, 2023, which corresponds to Chinese Patent Application No. 201980049253.9 and is related to U.S. Appl. No. 17/155,477; with English language translation.

\* cited by examiner

ULTRASOUND PROBE

CROSS-REFERENCE TO RELATED APPLICATIONS

This application is a Continuation of PCT International Application No. PCT/JP2019/028521 filed on Jul. 19, 2019, which claims priority under 35 U.S.C. § 119(a) to Japanese Patent Application No. 2018-139274 filed on Jul. 25, 2018. Each of the above applications is hereby expressly incorporated by reference, in its entirety, into the present application.

BACKGROUND OF THE INVENTION

1. Field of the Invention

The present invention relates to an ultrasound probe, and in particular, to an ultrasound probe that is connected to a diagnostic apparatus body through wireless communication.

2. Description of the Related Art

Hitherto, in a medical field, an ultrasound diagnostic apparatus using an ultrasound image has come into practical use. In general, this kind of ultrasound diagnostic apparatus has an ultrasound probe that incorporates a transducer array, and an apparatus body connected to the ultrasound probe. The ultrasound probe transmits ultrasonic waves toward a subject and receives ultrasound echoes from the subject, and the apparatus body electrically processes reception signals to generate an ultrasound image.

In recent years, for example, as disclosed in JP2015-211726A, a wireless ultrasound probe that is connected to a diagnostic apparatus body through wireless communication has been developed.

Such a wireless ultrasound probe transmits reception signals output from the transducer array to the diagnostic apparatus body through wireless communication or incorporates a circuit that performs signal processing, executes digital processing on the reception signals output from the transducer array, and transmits the reception signals to the diagnostic apparatus body through the wireless communication. The diagnostic apparatus body generates and displays an ultrasound image based on the signals transmitted from the ultrasound probe in a wireless manner.

SUMMARY OF THE INVENTION

In general, the wireless ultrasound probe disclosed in JP2015-211726A incorporates a battery as a drive power supply in many cases. In this way, in a case where the battery is incorporated in the ultrasound probe, and electric power that is supplied from the battery to each circuit in the ultrasound probe increases, there is demand for providing a fire protection measure for the ultrasound probe.

The invention has been accomplished in order to solve such a problem of the related art, and an object of the invention is to provide an ultrasound probe capable of exhibiting an excellent fire protection function.

In order to achieve the above-described object, an aspect of the invention provides an ultrasound probe comprising a housing, a transducer array that is retained in the housing and has a rear surface portion, from which a wiring cable is drawn out, a circuit substrate that is retained in the housing, the wiring cable being connected to the circuit substrate, a battery that is retained in the housing and performs power supply, and a fire protection structure disposed between the transducer array and the circuit substrate in the housing.

It is preferable that the fire protection structure has a rib that protrudes from an inner surface of the housing and separates between the rear surface portion of the transducer array and the circuit substrate, and an opening portion into which the wiring cable is inserted is formed in the rib.

In this case, it is preferable that a gap between the opening portion and the wiring cable is blocked by a flame retardant member.

Alternatively, the fire protection structure may have a flame retardant member disposed inside the housing to separate between the rear surface portion of the transducer array and the circuit substrate.

In this case, it is preferable that the flame retardant member is formed of flame retardant sponge that blocks between an inner surface of the housing and the wiring cable.

It is preferable that the flame retardant sponge contains silicone resin or urethane resin.

Alternatively, the flame retardant member may be formed of flame retardant resin molded inside the housing such that the wiring cable is inserted.

In this case, it is preferable that the flame retardant resin is formed of modified polyphenylene ether resin or polycarbonate/acrylonitrile-butadiene-styrene alloy resin.

Alternatively, the flame retardant member may be formed of a metal block into which the wiring cable is inserted.

In this case, it is preferable that the metal block is formed of aluminum.

The metal block may be in contact with the rear surface portion of the transducer array.

Alternatively, the flame retardant member may be formed of sheet-shaped flame retardant resin pasted to the rear surface portion of the transducer array.

The housing may be formed of modified polyphenylene ether resin or polycarbonate/acrylonitrile-butadiene-styrene alloy resin.

According to the aspect of the invention, the ultrasound probe comprises the transducer array that is retained in the housing and has the rear surface portion, from which the wiring cable is drawn out, the circuit substrate that is retained in the housing, the wiring cable being connected to the circuit substrate, the battery that is retained in the housing and performs power supply, and the fire protection structure disposed between the transducer array and the circuit substrate in the housing. Thus, it is possible to exhibit an excellent fire protection function.

DESCRIPTION OF THE PREFERRED EMBODIMENTS

Hereinafter, embodiments of the invention will be described referring to the accompanying drawings.

Embodiment 1

Figure 1:
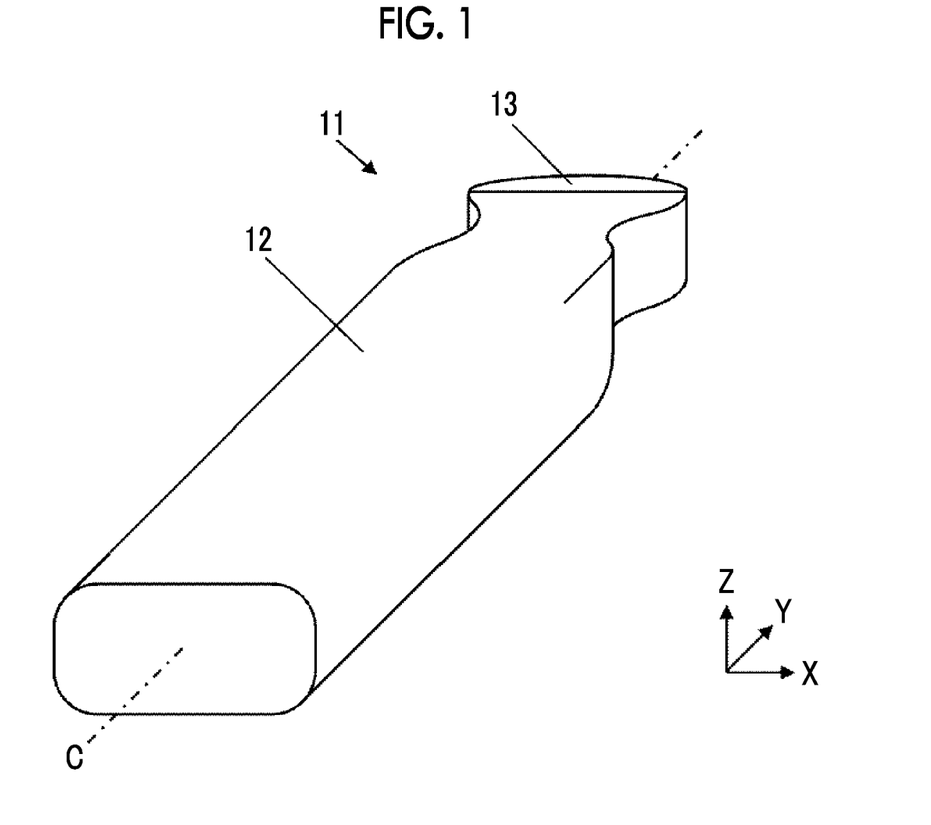
FIG. 1 is a perspective view of an ultrasound probe according to Embodiment 1 of the invention.

FIG. 1 shows an ultrasound probe 11 according to Embodiment 1 of the invention. As shown in FIG. 1, the ultrasound probe 11 has a housing 12 having a substantially prismatic shape around a center axis C, and a transducer array 13 disposed at one end of the housing 12. The housing 12 is formed of, for example, an insulating resin material having flame retardance, such as modified polyphenylene ether (m-PPE) or polycarbonate/acrylonitrile-butadiene-styrene alloy (PC/ABS alloy). Here, as a resin material having flame retardance, for example, a resin material having flame retardance of a flame retardant grade V-1, V-0, 5VB, or 5VA defined in the UL94 standard is preferably used. The UL94 standard is a standard for evaluation of flame retardance established by Underwriters Laboratories Inc.

Hereinafter, for description, a direction parallel to a center axis is referred to as a Y direction, a width direction perpendicular to the Y direction is referred to as an X direction, and a height direction perpendicular to the X direction and the Y direction is referred to as a Z direction.

As described below, the ultrasound probe 11 transmits and receives ultrasonic waves to and from a subject with the transducer array 13 to capture an ultrasound image representing a tomographic plane of the subject, and is connected to a diagnostic apparatus body, which generates and displays the ultrasound image based on signals acquired by the ultrasound probe 11, through wireless communication. As described below, the ultrasound probe 11 incorporates a battery, and electric power is supplied to each circuit of the ultrasound probe 11 by the incorporated battery.

Figure 2:
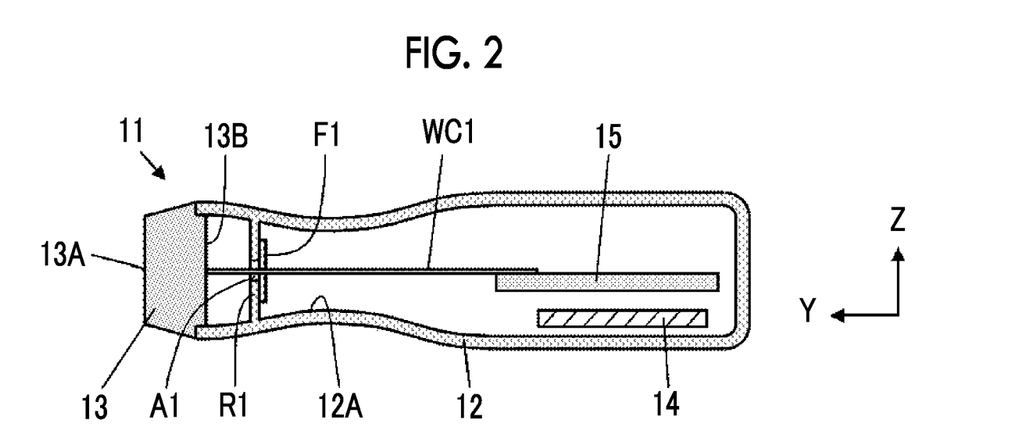
FIG. 2 is a side cross-sectional view of the ultrasound probe according to Embodiment 1 of the invention.

FIG. 2 is a side cross-sectional view of the ultrasound probe 11 taken along a surface that passes through a center axis C and is parallel to a YZ plane. As shown in FIG. 2, the ultrasound probe 11 incorporates a battery 14 and a circuit substrate 15 electrically connected to the battery 14, and one end of a wiring cable WC1 is connected to the circuit substrate 15. A transducer array 13 is connected to the other end of the wiring cable WC1. The transducer array 13 has a front surface portion 13A that is exposed outside the housing 12 and is brought into contact with a body surface of the subject during ultrasound diagnosis, and a rear surface portion 13B that is accommodated inside the housing 12, and the wiring cable WC1 is drawn out from the rear surface portion 13B of the transducer array 13.

Figure 3:
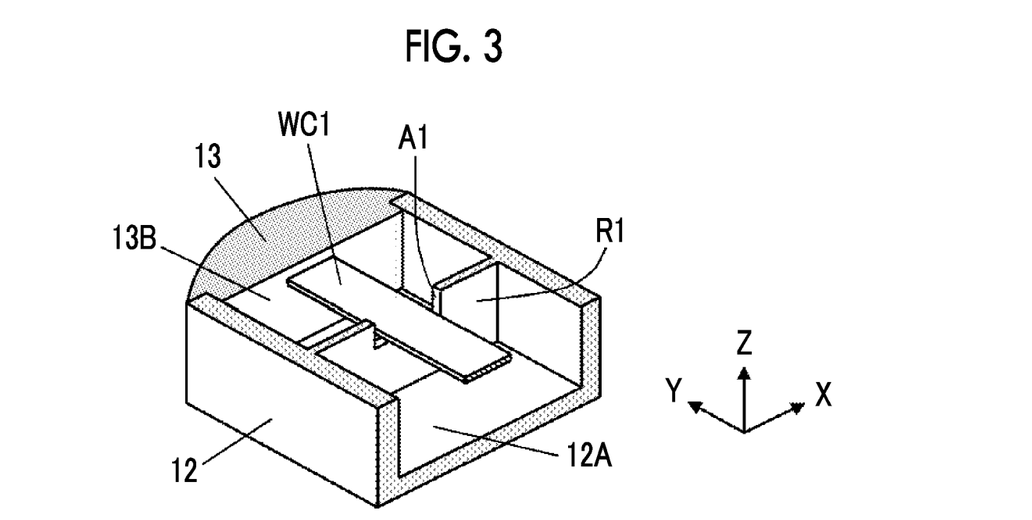
FIG. 3 is a perspective cross-sectional view of the ultrasound probe according to Embodiment 1 of the invention.

The housing 12 has a rib R1 that protrudes from an inner surface 12A of the housing 12 and separates between the rear surface portion 13B of the transducer array 13 and the circuit substrate 15. As shown in FIGS. 2 and 3, the rib R1 has a plate shape in which a rectangular opening portion A1 is formed in a center portion, and the wiring cable WC1 drawn out from the rear surface portion 13B of the transducer array 13 is inserted into the opening portion A1 of the rib R1. As shown in FIG. 2, sheet-shaped flame retardant resin F1 is adhered to the rib R1 to block a gap between the opening portion A1 and the wiring cable WC1. The sheet-shaped flame retardant resin F1 preferably has flame retardance of, for example, V-1 or more in the UL94 standard, and a polyethylene terephthalate film or the like to which a so-called flame retardant is added is used. For example, the sheet-shaped flame retardant resin F1 is adhered to the rib R1 by an adhesive. Here, FIG. 3 is a perspective cross-sectional view of the ultrasound probe 11 taken along a surface parallel to an XY plane and a surface parallel to an XZ plane. For description, the sheet-shaped flame retardant resin F1 is omitted.

Here, in an ultrasound probe that incorporates a battery as a drive power supply, in a case where electric power that is supplied from the battery increases, it is desirable that a fire protection measure is provided for the ultrasound probe. However, normally, a material constituting the transducer array in the ultrasound probe is decided from acoustic performance, and thus, may not have flame retardance. That is, a fire protection measure may not be provided for the transducer array itself.

In the ultrasound probe 11 according to Embodiment 1, the transducer array 13 is separated from the battery 14 and the circuit substrate 15 by the rib R1 and the sheet-shaped flame retardant resin F1, and both of the battery 14 and the circuit substrate 15 are disposed in a space closed by the housing 12, the rib R1, and the sheet-shaped flame retardant resin F1 having flame retardance.

In this way, with the ultrasound probe 11 of Embodiment 1, even though the transducer array 13 does not have flame retardance, the transducer array 13 is separated from the battery 14 and the circuit substrate 15 by a fire protection structure constituted of the rib R1 and the sheet-shaped flame retardant resin F1. Thus, it is possible to exhibit an excellent fire protection function.

Figure 4:
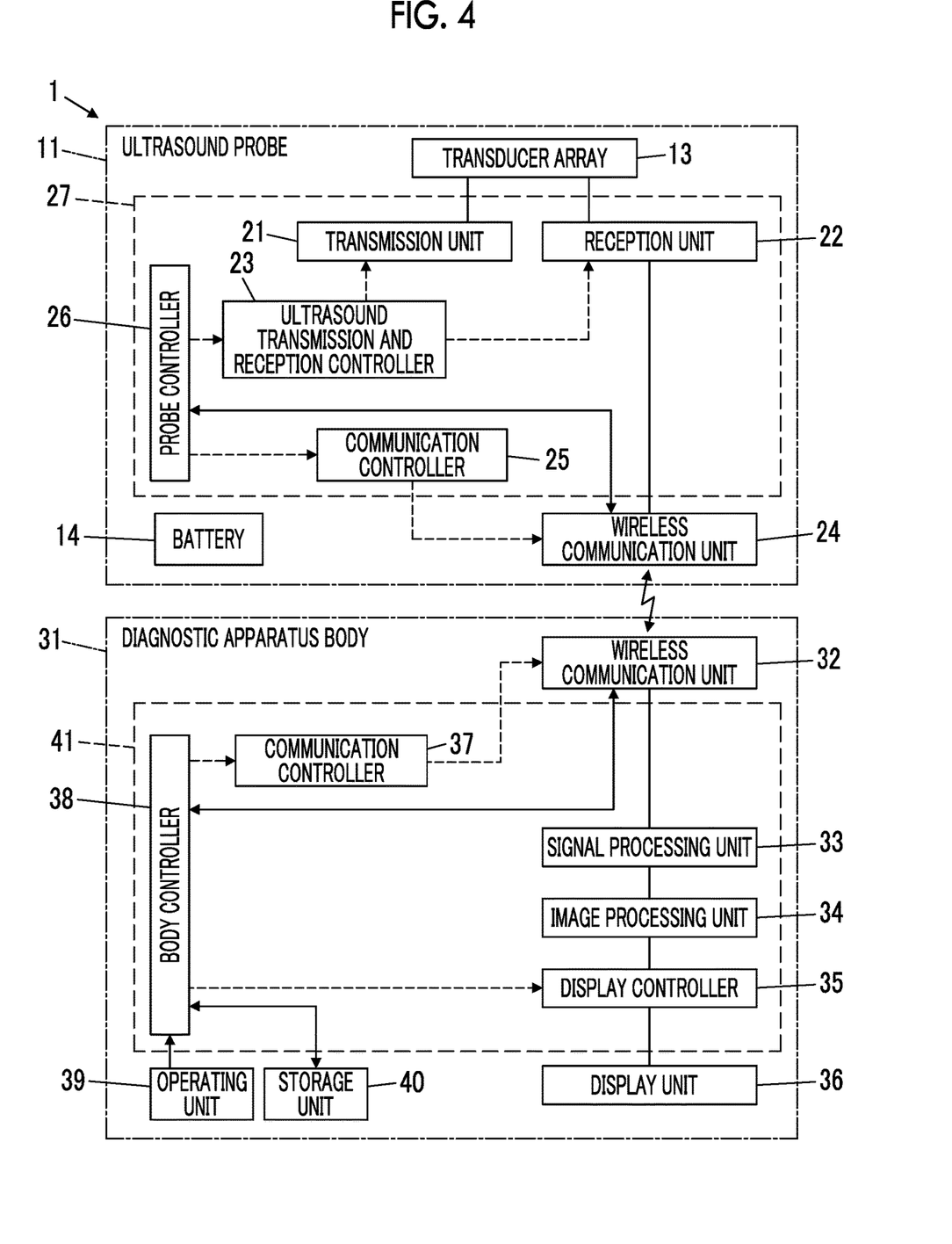
FIG. 4 is a block diagram showing the configuration of an ultrasound diagnostic apparatus comprising the ultrasound probe according to Embodiment 1 of the invention.

Next, an ultrasound diagnostic apparatus 1 comprising the ultrasound probe 11 according to Embodiment 1 of the invention will be described. FIG. 4 shows the configuration of the ultrasound diagnostic apparatus 1. As shown in FIG. 4, the ultrasound diagnostic apparatus 1 comprises the ultrasound probe 11 according to Embodiment 1 of the invention and a diagnostic apparatus body 31, and the ultrasound probe 11 and the diagnostic apparatus body 31 are connected through wireless communication.

The ultrasound probe 11 comprises the transducer array 13, and a transmission unit 21 and a reception unit 22 are connected to the transducer array 13. An ultrasound transmission and reception controller 23 is connected to the transmission unit 21 and the reception unit 22. A wireless communication unit 24 is connected to the reception unit 22, and a communication controller 25 is connected to the wireless communication unit 24. A probe controller 26 is connected to the ultrasound transmission and reception controller 23, the wireless communication unit 24, and the communication controller 25. Here, the wireless communication unit 24 and the probe controller 26 are connected in such a manner that information can be transferred in two directions. The ultrasound probe 11 incorporates the battery 14.

The transmission unit 21, the reception unit 22, the ultrasound transmission and reception controller 23, the communication controller 25, and the probe controller 26 constitute an ultrasound probe-side processor 27.

The diagnostic apparatus body 31 comprises a wireless communication unit 32, and a signal processing unit 33, an image processing unit 34, a display controller 35, and a display unit 36 are sequentially connected to the wireless communication unit 32. A communication controller 37 is connected to the wireless communication unit 32, and a body controller 38 is connected to the wireless communication unit 32, the communication controller 37, and the display controller 35. An operating unit 39 and a storage unit 40 are connected to the body controller 38. Here, the wireless communication unit 32 and the body controller 38, and the body controller 38 and the storage unit 40 are connected in such a manner that information can be transferred in two directions.

The signal processing unit 33, the image processing unit 34, the display controller 35, the communication controller 37, and the body controller 38 constitute a diagnostic apparatus body-side processor 41.

The wireless communication unit 24 of the ultrasound probe 11 and the wireless communication unit 32 of the diagnostic apparatus body 31 are connected in such a manner that information can be transferred in two directions. With this, the ultrasound probe 11 and the diagnostic apparatus body 31 are connected through wireless communication.

The transducer array 13 of the ultrasound probe 11 shown in FIG. 4 has a plurality of transducers arranged in a one-dimensional or two-dimensional manner. The transducers transmit ultrasonic waves in compliance with drive signals supplied from the transmission unit 21, receive ultrasound echoes from the subject, and output reception signals. Each transducer is constituted by forming electrodes at both ends of a piezoelectric body formed of, for example, piezoelectric ceramic represented by lead zirconatetitanate (PZT), a polymer piezoelectric element represented by poly vinylidene di fluoride (PVDF), piezoelectric single crystal represented by lead magnesium niobate-lead titanate (PMN-PT), or the like.

The ultrasound transmission and reception controller 23 of the ultrasound probe-side processor 27 performs control such that the transmission unit 21 and the reception unit 22 perform transmission of an ultrasonic beam and reception of ultrasound echoes based on an instruction from the probe controller 26, respectively.

The transmission unit 21 of the ultrasound probe-side processor 27 includes, for example, a plurality of pulse generators, and adjusts a delay amount of each drive signal based on a transmission delay pattern selected according to a control signal from the ultrasound transmission and reception controller 23 such that ultrasonic waves transmitted from a plurality of transducers of the transducer array 13 form an ultrasonic beam, and supplies the drive signals to a plurality of transducers. In this way, in a case where a pulsed or continuous-wave voltage is applied to the electrodes of each of a plurality of transducers of the transducer array 13, the piezoelectric body expands and contracts to generate a pulsed or continuous-wave ultrasonic wave from each of the transducers. An ultrasonic beam is formed from a combined wave of the ultrasonic waves.

The transmitted ultrasonic beam is reflected by, for example, a target, such as a part of the subject, and propagates toward the transducer array 13 of the ultrasound probe 11. The ultrasound echoes that propagate toward the transducer array 13 in this way are received by the respective transducers constituting the transducer array 13. In this case, each of the transducers constituting the transducer array 13 expands and contracts with reception of the propagating ultrasound echo to generate an electrical signal, and outputs the electrical signal to the reception unit 22.

Figure 5:
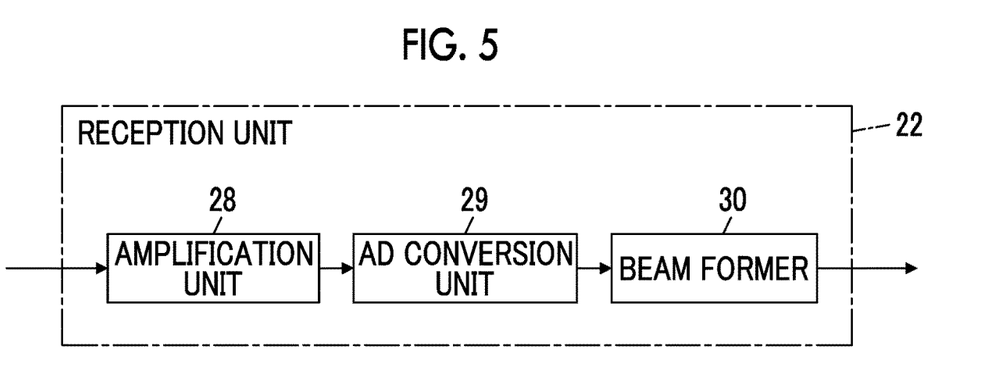
FIG. 5 is a block diagram showing the internal configuration of a reception unit in Embodiment 1 of the invention.

The reception unit 22 of the ultrasound probe-side processor 27 executes processing of the reception signals output from the transducer array 13 in compliance with a control signal from the ultrasound transmission and reception controller 23. As shown in FIG. 5, the reception unit 22 has a configuration in which an amplification unit 28, an analog-to-digital (AD) conversion unit 29, and a beamformer 30 are connected in series. The amplification unit 28 amplifies the reception signal input from each of the transducers constituting the transducer array 13 and transmits the amplified reception signal to the AD conversion unit 29. The AD conversion unit 29 converts the reception signal transmitted from the amplification unit 28 into digitized data and sends the digitized data to the beamformer 30. The beamformer 30 executes reception focus processing of giving a delay to each piece of data compliant with a set sound speed based on a reception delay pattern selected according to a control signal from the ultrasound transmission and reception controller 23 and performing addition (phasing addition). With the reception focus processing, a sound ray signal in which a focus of the ultrasound echo is narrowed on a given scanning line is generated. The sound ray signal generated in this manner is sent to the wireless communication unit 24 of the ultrasound probe 11.

The wireless communication unit 24 of the ultrasound probe 11 includes an antenna that performs transmission and reception of radio waves, and performs wireless communication with the wireless communication unit 32 of the diagnostic apparatus body 31. In this case, the wireless communication unit 24 modulates a carrier based on the sound ray signal sent from the reception unit 22 to generate a transmission signal and transmits the generated transmission signal to the wireless communication unit 32 of the diagnostic apparatus body 31 in a wireless manner. As a modulation system of the carrier, for example, amplitude shift keying (ASK), phase shift keying (PSK), quadrature phase shift keying (QPSK), 16 quadrature amplitude modulation (16QAM), or the like is used.

The communication controller 25 of the ultrasound probe-side processor 27 performs control such that the wireless communication unit 24 of the ultrasound probe 11 transmits the sound ray signal with transmission field intensity set by the probe controller 26.

The probe controller 26 of the ultrasound probe-side processor 27 performs control of each unit of the ultrasound probe 11 based on a program or the like stored in advance.

The battery 14 of the ultrasound probe 11 is incorporated in the ultrasound probe 11, and supplies electric power to each circuit of the ultrasound probe 11.

The wireless communication unit 32 of the diagnostic apparatus body 31 includes an antenna that performs transmission and reception of radio waves, and performs wireless communication with the wireless communication unit 24 of the ultrasound probe 11. In this case, the wireless communication unit 32 of the diagnostic apparatus body 31 outputs a sound ray signal, for example, by receiving the transmission signal transmitted from the wireless communication unit 24 of the ultrasound probe 11 through the antenna in a wireless manner and demodulating the received transmission signal. The wireless communication unit 32 of the diagnostic apparatus body 31 sends the sound ray signal output in this manner to the signal processing unit 33.

The signal processing unit 33 of the diagnostic apparatus body-side processor 41 performs correction of attenuation of the sound ray signal sent from the wireless communication unit 32 due to a propagation distance according to a depth of a reflection position of the ultrasonic wave, and then, executes envelope detection to generate a signal as tomographic image information regarding a tissue in the subject.

The image processing unit 34 of the diagnostic apparatus body-side processor 41 generates an ultrasound image signal by raster-converting the signal generated by the signal processing unit 33 into an image signal in compliance with a normal television signal scanning system and executing various kinds of necessary image processing, such as brightness correction, gradation correction, sharpness correction, and color correction, on the image signal generated in this manner. The image processing unit 34 sends the ultrasound image signal generated in this manner to the display controller 35.

The display controller 35 of the diagnostic apparatus body-side processor 41 executes predetermined processing on the ultrasound image signal generated by the image processing unit 34 and displays an ultrasound image on the display unit 36 under the control of the body controller 38.

The display unit 36 of the diagnostic apparatus body 31 displays an image under the control of the display controller 35, and includes, for example, a display device, such as a liquid crystal display (LCD), an organic electroluminescence display (organic EL display).

The communication controller 37 of the diagnostic apparatus body-side processor 41 performs control such that the wireless communication unit 32 of the diagnostic apparatus body 31 receives the transmission signal from the wireless communication unit 24 of the ultrasound probe 11.

The body controller 38 of the diagnostic apparatus body-side processor 41 performs control of each unit of the diagnostic apparatus body 31 based on a program stored in advance in the storage unit 40 or the like and a user's operation through the operating unit 39.

The operating unit 39 of the diagnostic apparatus body 31 is provided for the user to perform an input operation, and can comprise a keyboard, a mouse, a trackball, a touch pad, a touch panel, and the like.

The storage unit 40 of the diagnostic apparatus body 31 stores an operation program and the like of the diagnostic apparatus body 31, and as the storage unit 40, a recording medium, such as a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory), a server, or the like can be used.

Here, in the ultrasound probe 11, the ultrasound probe-side processor 27 having the transmission unit 21, the reception unit 22, the ultrasound transmission and reception controller 23, the communication controller 25, and the probe controller 26, and the diagnostic apparatus body-side processor 41 having the signal processing unit 33, the image processing unit 34, the display controller 35, the communication controller 37, and the body controller 38 are constituted of a central processing unit (CPU) and a control program causing the CPU to execute various kinds of processing. However, the ultrasound probe-side processor 27 and the diagnostic apparatus body-side processor 41 may be constituted using a field programmable gate array (FPGA), a digital signal processor (DSP), an application specific integrated circuit (ASIC), a graphics processing unit (GPU), or other integrated circuits (ICs) or may be constituted by combining the IC circuits.

The transmission unit 21, the reception unit 22, the ultrasound transmission and reception controller 23, the communication controller 25, and the probe controller 26 of the ultrasound probe-side processor 27 may be constituted to be partially or wholly integrated into one CPU or the like. The signal processing unit 33, the image processing unit 34, the display controller 35, the communication controller 37, and the body controller 38 of the diagnostic apparatus body-side processor 41 may be constituted to be partially or wholly integrated into one CPU or the like.

In Embodiment 1, as shown in FIG. 1, although the housing 12 has a substantially prismatic shape, the shape of the housing 12 is not particularly limited. For example, the housing may have a columnar shape.

The wiring cable WC1 that is connected to the transducer array 13 and the circuit substrate 15 is not particularly limited as long as electric conduction is provided. For example, a flexible print substrate or the like is used as the wiring cable WC1.

In Embodiment 1, although the opening portion A1 formed in the rib R1 of the housing 12 has a rectangular shape and is formed in the center portion of the rib R1, the shape and the forming position of the opening portion A1 are not particularly limited. For example, the opening portion A1 of the rib R1 may have a circular shape, a polygonal shape, or any other shapes as long as the wiring cable WC1 can be inserted thereinto. The opening portion A1 may be formed in an end portion, a corner portion, or the like of the rib R1, not in the center portion of the rib R1.

Figure 6:
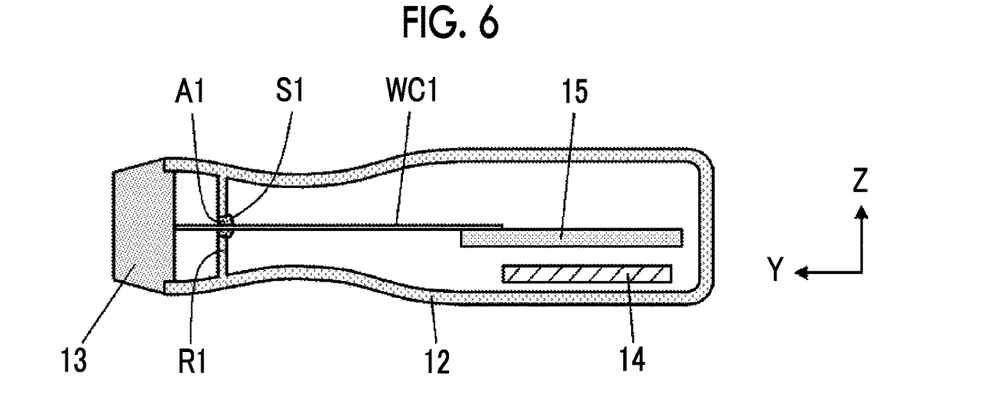
FIG. 6 is a side cross-sectional view of an ultrasound probe according to a modification example of Embodiment 1 of the invention.

In Embodiment 1, although the gap between the opening portion A1 formed in the rib R1 of the housing 12 and the wiring cable WC1 is blocked by the sheet-shaped flame retardant resin F1, the gap may be blocked by any member having flame retardance. For example, as shown in FIG. 6, the gap between the opening portion A1 of the rib R1 and the wiring cable WC1 may be blocked by flame retardant sponge S1. In this case, for example, the flame retardant sponge S1 is adhered to the rib R1 by an adhesive. Here, as the flame retardant sponge S1, for example, sponge formed of silicone resin, urethane resin, or the like having flame retardance of V-1 or more in the UL94 standard is used. Even in this case, similarly to a case where the gap between the opening portion A1 of the rib R1 and the wiring cable WC1 is blocked by the sheet-shaped flame retardant resin F1, the transducer array 13 is separated from the battery 14 and the circuit substrate 15 by a fire protection structure. Thus, it is possible to exhibit an excellent fire protection function.

Figure 7:
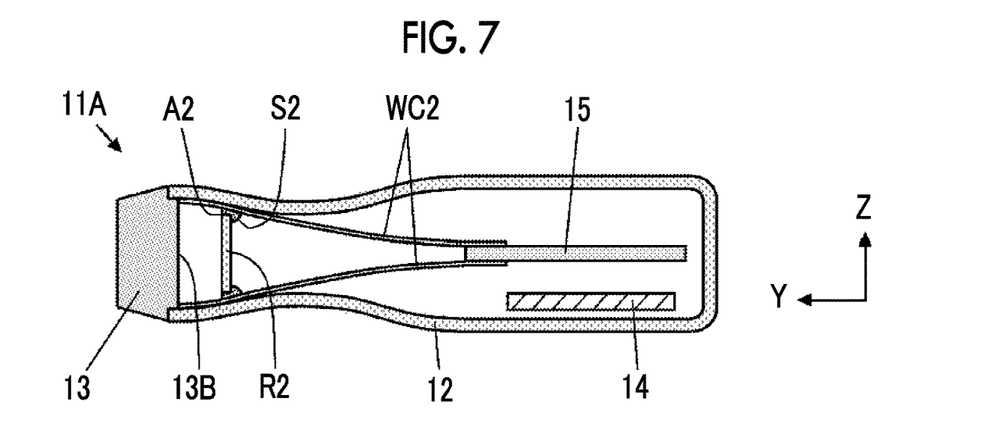
FIG. 7 is a side cross-sectional view of an ultrasound probe according to another modification example of Embodiment 1 of the invention.
Figure 8:
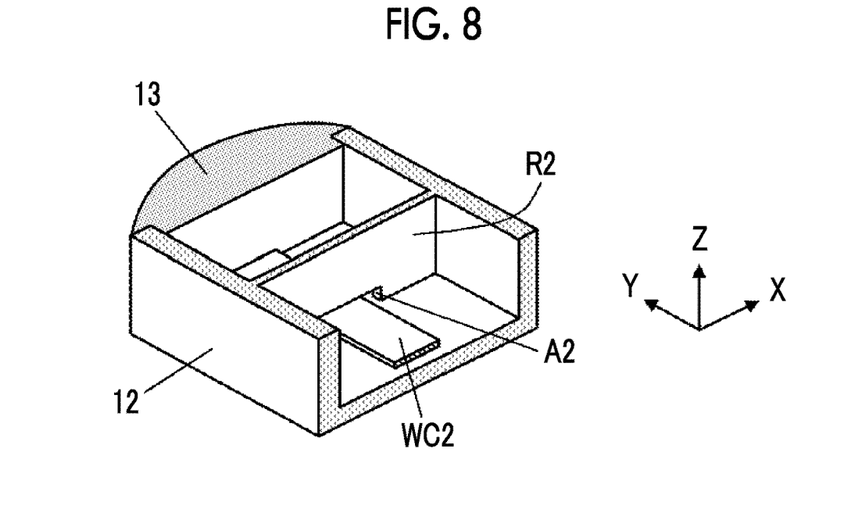
FIG. 8 is a perspective cross-sectional view of the ultrasound probe shown in FIG. 7.

In Embodiment 1, although one wiring cable WC1 is drawn out from the rear surface portion 13B of the transducer array 13, as shown in FIG. 7, two wiring cables WC2 may be drawn out from the transducer array 13. FIG. 7 shows an ultrasound probe 11A according to a modification example of Embodiment 1. In the ultrasound probe 11A, a pair of wiring cables WC2 is drawn out from both end portions of the rear surface portion 13B of the transducer array 13 in the Z direction, and a pair of wiring cables WC2 is connected to the circuit substrate 15. As shown in FIGS. 7 and 8, rectangular opening portions A2 are formed in both end portions of a rib R2 of the housing 12 in the Z direction, and a gap between each of the opening portions A2 and each of the wiring cables WC2 is blocked by flame retardant sponge S2. Here, in FIG. 8, for description, the flame retardant sponge S2 is omitted.

In this way, the transducer array 13 is separated from the battery 14 and the circuit substrate 15 by a fire protection structure constituted of the rib R2 of the housing 12 and the flame retardant sponge S2, and the battery 14 and the circuit substrate 15 are disposed in a closed space formed by the housing 12, the rib R2, and the flame retardant sponge S2.

Accordingly, even though a plurality of wiring cables are drawn out from the rear surface portion 13B of the transducer array 13, the transducer array 13 is separated from the battery 14 and the circuit substrate 15 by flame retardant members, such as the rib R2 of the housing 12 and the flame retardant sponge S2. Thus, similarly to the ultrasound probe 11 of Embodiment 1, it is possible to exhibit an excellent fire protection function.

Embodiment 2

In Embodiment 1, the fire protection structure is constituted of the rib R1 of the housing 12 and the sheet-shaped flame retardant resin F1 that blocks the gap between the opening portion A1 of the rib R1 and the wiring cable WC1. In contrast, a fire protection structure may be constituted by disposing a flame retardant member between the transducer array 13 and the parts of the battery 14 and the circuit substrate 15.

Figure 9:
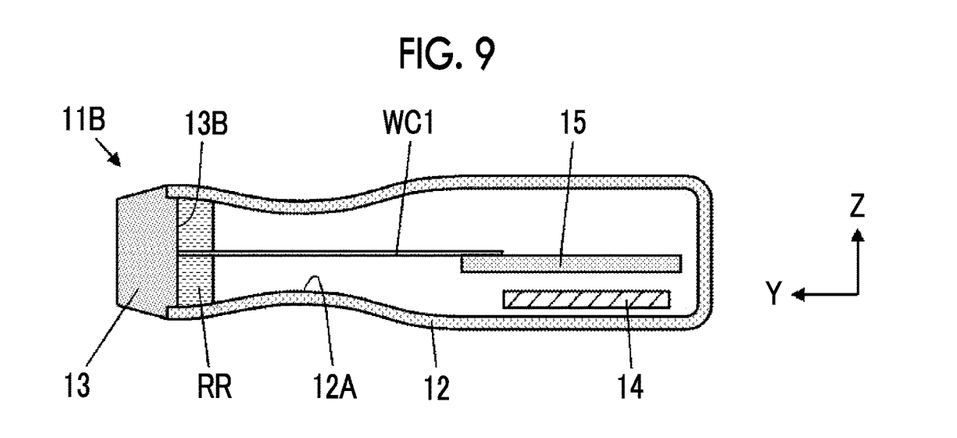
FIG. 9 is a side cross-sectional view of an ultrasound probe according to Embodiment 2 of the invention.

FIG. 9 shows an ultrasound probe 11B according to Embodiment 2. In the ultrasound probe 11B, flame retardant resin RR is disposed as a flame retardant member to separate the transducer array 13 from the battery 14 and the circuit substrate 15. The flame retardant resin RR preferably has flame retardance of, for example, V-1 or more in the UL94 standard, and is formed of m-PPE resin, PC/ABS alloy resin, epoxy resin, urethane resin, or the like. The flame retardant resin RR is closely attached to the rear surface portion 13B of the transducer array 13, a part of the inner surface 12A of the housing 12, and a part of the wiring cable WC1 by, for example, cast molding, fixing with an adhesive, or the like.

Accordingly, with the ultrasound probe 11B according to Embodiment 2, the transducer array 13 is separated from the battery 14 and the circuit substrate 15 by the flame retardant resin RR. Thus, a fire protection structure is constituted of the flame retardant resin RR, and similarly to the ultrasound probe 11 of Embodiment 1, it is possible to exhibit an excellent fire protection function.

In Embodiment 2, although the flame retardant resin RR is closely attached to the rear surface portion 13B of the transducer array 13, the flame retardant resin RR may be disposed away from the transducer array 13 as long as the transducer array 13 is separated from the battery 14 and the circuit substrate 15.

Figure 10:
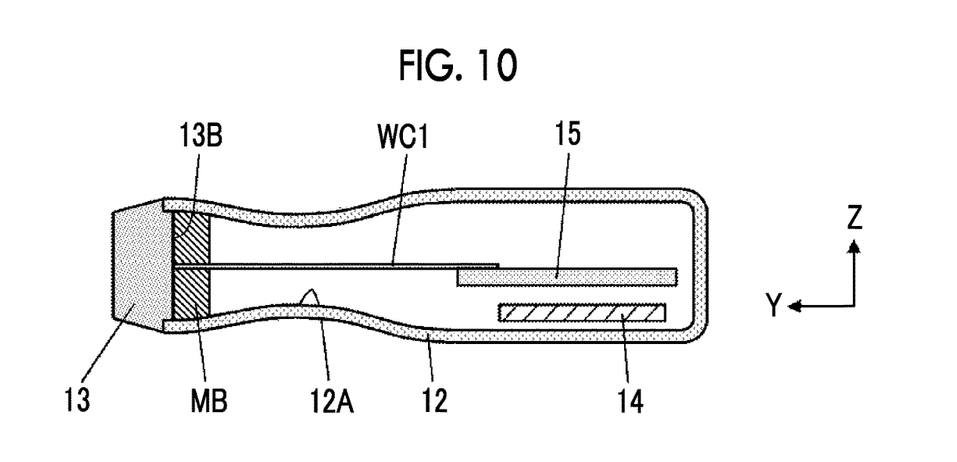
FIG. 10 is a side cross-sectional view of an ultrasound probe according to a first modification example of Embodiment 2 of the invention.

In Embodiment 2, although the flame retardant resin RR is used as a flame retardant member constituting a fire protection structure, the invention is not particularly limited thereto. For example, as in a first modification example shown in FIG. 10, a metal block MB may be used as a flame retardant member. A material constituting the metal block MB is not particularly limited, and for example, the metal block MB may be formed of a metal having high thermal conductivity, such as aluminum. In a case where the metal block MB having high thermal conductivity is in contact with the rear surface portion 13B of the transducer array 13 as shown in FIG. 10, not only the metal block MB can reliably provide fire protection for the inside of the ultrasound probe, but also the metal block MB can absorb heat generated in the transducer array 13 due to the operation of the ultrasound probe to restrain an increase in temperature of the transducer array 13.

Figure 11:
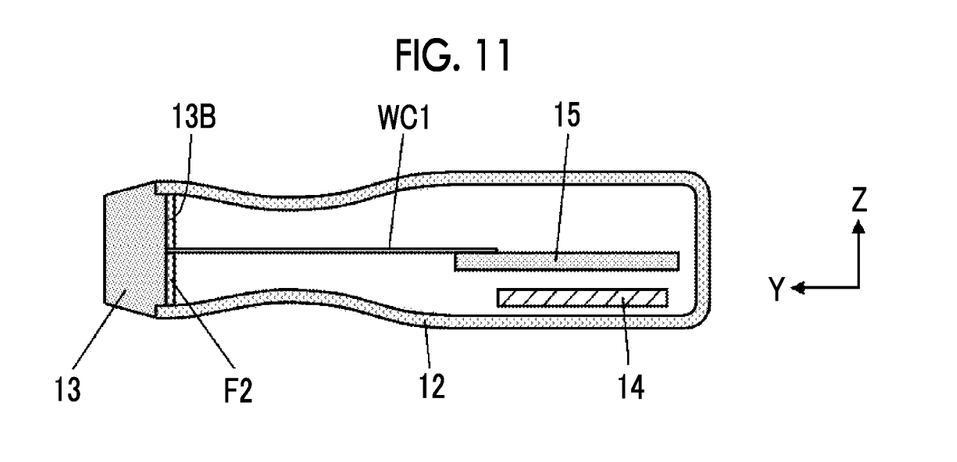
FIG. 11 is a side cross-sectional view of an ultrasound probe according to a second modification example of Embodiment 2 of the invention.

For example, as in a second modification example shown in FIG. 11, sheet-shaped flame retardant resin F2 may be used as a flame retardant member constituting a fire protection structure. In the example shown in FIG. 11, the sheet-shaped flame retardant resin F2 is adhered to the entire surface of the rear surface portion 13B of the transducer array 13, and constitutes a fire protection structure that separates the transducer array 13 from the battery 14 and the circuit substrate 15. In this way, in a case where the sheet-shaped flame retardant resin F2 is used as a flame retardant member, the sheet-shaped flame retardant resin F2 is adhered to the entire surface of the rear surface portion 13B of the transducer array 13, whereby it is possible to easily constitute a fire protection structure.

Figure 12:
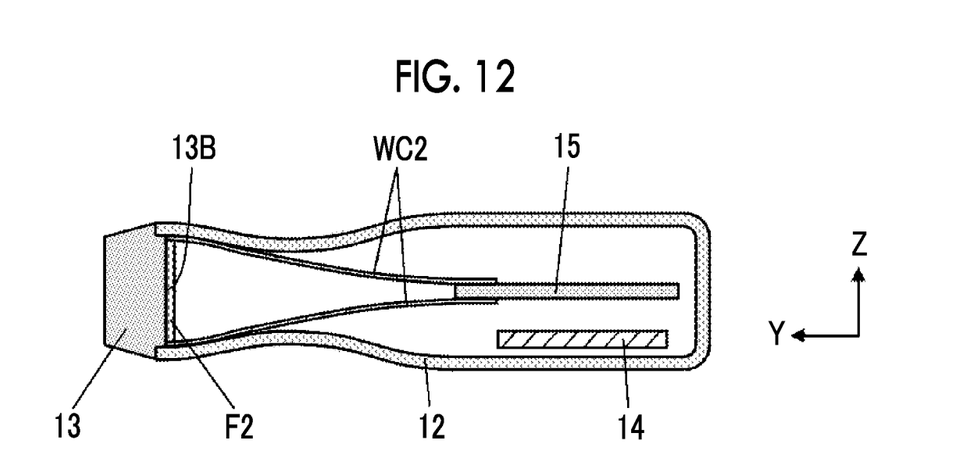
FIG. 12 is a side cross-sectional view of an ultrasound probe according to a third modification example of Embodiment 2 of the invention.

In the second modification example shown in FIG. 11, one wiring cable WC1 is drawn out from the rear surface portion 13B of the transducer array 13. However, as in a third modification example shown in FIG. 12, even though two wiring cables WC2 are drawn out from the rear surface portion 13B of the transducer array 13, similarly, it is possible to easily constitute a fire protection structure with the sheet-shaped flame retardant resin F2.

Figure 13:
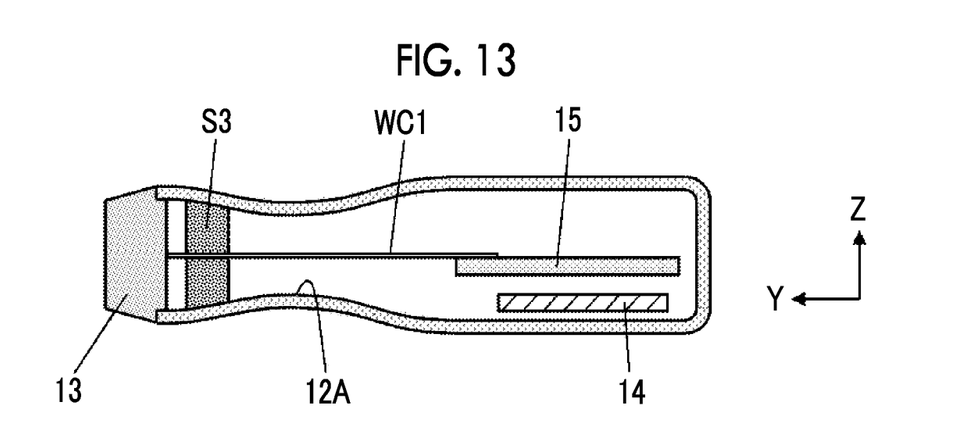
FIG. 13 is a side cross-sectional view of an ultrasound probe according to a fourth modification example of Embodiment 2 of the invention.

For example, as in a fourth modification example shown in FIG. 13, flame retardant sponge S3 may be used as a flame retardant member constituting a fire protection structure. In this case, the flame retardant sponge S3 can be fixed to, for example, the inner surface 12A of the housing 12, by an adhesive, a double-sided tape, or the like. In this case, in a case where the flame retardant sponge S3 is used as a flame retardant member, the flame retardant sponge S3 is adhered to the inner surface 12A of the housing 12 to separate the transducer array 13 from the battery 14 and the circuit substrate 15, whereby it is possible to easily constitute a fire protection structure.

Figure 14:
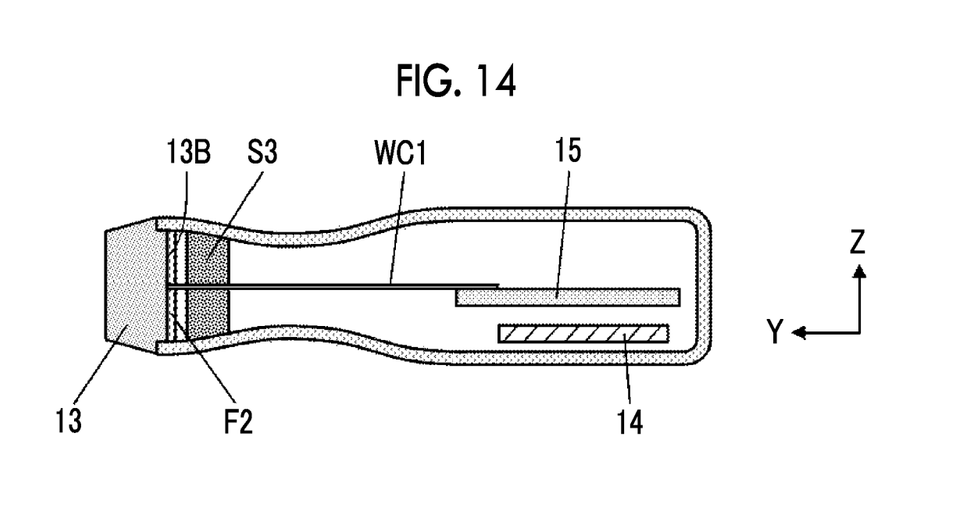
FIG. 14 is a side cross-sectional view of an ultrasound probe according to a fifth modification example of Embodiment 2 of the invention.

For example, a fire protection structure may be constituted by disposing a plurality of flame retardant members between the transducer array 13 and the parts of the battery 14 and the circuit substrate 15. For example, as in a fifth modification example shown in FIG. 14, sheet-shaped flame retardant resin F2 can be adhered to the entire surface of the rear surface portion 13B of the transducer array 13, and flame retardant sponge S3 can be disposed between the sheet-shaped flame retardant resin F2 and the parts of the battery 14 and the circuit substrate 15. With this, it is possible to more reliably provide fire protection for the inside of the ultrasound probe.

EXPLANATION OF REFERENCES

1: ultrasound diagnostic apparatus
11, 11A, 11B: ultrasound probe
12: housing
12A: inner surface
13: transducer array
13A: front surface portion
13B: rear surface portion
14: battery
15: circuit substrate
A1, A2: opening portion
C: center axis F1, F2: sheet-shaped flame retardant resin
MB: metal block
R1, R2: rib
RR: flame retardant resin
S1, S2, S3: flame retardant sponge
WC1, WC2: wiring cable.

What is claimed is:

1. An ultrasound probe comprising:
a housing;
a transducer array that is retained by the housing and has a rear surface portion, from which a wiring cable is drawn out and a remaining surface portion except the rear surface portion;
a circuit substrate that is retained in the housing, the wiring cable being connected to the circuit substrate;
a battery that is retained in the housing and performs power supply; and
a fire protection structure disposed between the transducer array and the circuit substrate in the housing,
wherein the rear surface portion of the transducer array is disposed inside the housing and the remaining surface portion of the transducer array is disposed outside the housing,
the fire protection structure has a first flame retardant member separating between the rear surface portion and the circuit substrate,
the first flame retardant member is arranged to fill a gap between the housing and the transducer array, and
a closed space is defined by the housing, the rear surface portion of the transducer array, and the first flame retardant member.

2. The ultrasound probe according to claim 1,
wherein the first flame retardant member is composed of a rib that protrudes from an inner surface of the housing and separates between the rear surface portion of the transducer array and the circuit substrate, and a second flame retardant member adhered to the rib,
an opening portion into which the wiring cable is inserted is formed in the rib, and
a gap between the opening portion and the wiring cable is blocked by the second flame retardant member.

3. The ultrasound probe according to claim 2,
wherein the housing is formed of modified polyphenylene ether resin or polycarbonate/acrylonitrile-butadiene-styrene alloy resin.

4. The ultrasound probe according to claim 1,
wherein the fire protection structure has a flame retardant sponge that blocks between an inner surface of the housing and the wiring cable.

5. The ultrasound probe according to claim 4,
wherein the flame retardant sponge contains silicone resin or urethane resin.

6. The ultrasound probe according to claim 1,
wherein the first flame retardant member is formed of flame retardant resin molded inside the housing such that the wiring cable is inserted.

7. The ultrasound probe according to claim 6,
wherein the flame retardant resin is formed of modified polyphenylene ether resin or polycarbonate/acrylonitrile-butadiene-styrene alloy resin.

8. The ultrasound probe according to claim 1,
wherein the first flame retardant member is formed of a metal block into which the wiring cable is inserted.

9. The ultrasound probe according to claim 8,
wherein the metal block is formed of aluminum.

10. The ultrasound probe according to claim 1,
wherein the housing is formed of modified polyphenylene ether resin or polycarbonate/acrylonitrile-butadiene-styrene alloy resin.

* * * * *